United States Patent
Starner et al.

(10) Patent No.: US 7,282,543 B2
(45) Date of Patent: Oct. 16, 2007

(54) POLYEPOXY RESIN COMPOSITIONS

(75) Inventors: William Edward Starner, Cherry Hill, NJ (US); John Phillip Cech, Moorestown, NJ (US)

(73) Assignee: CVC Specialty Chemical, Inc., Moorestown, NJ (US)

( * ) Notice: Subject to any disclaimer, the term of this patent is extended or adjusted under 35 U.S.C. 154(b) by 378 days.

(21) Appl. No.: 10/666,358

(22) Filed: Sep. 19, 2003

(65) Prior Publication Data

US 2005/0065317 A1    Mar. 24, 2005

(51) Int. Cl.
*C08L 63/00* (2006.01)
*B65D 85/00* (2006.01)

(52) U.S. Cl. .................... 525/533; 206/524.1
(58) Field of Classification Search ........... 525/533; 206/524.1
See application file for complete search history.

(56) References Cited

U.S. PATENT DOCUMENTS

| 4,014,830 | A | | 3/1977 | Rumfield | ............... 528/111.5 |
|---|---|---|---|---|---|
| 4,642,011 | A | * | 2/1987 | Uramoto et al. | ............ 411/258 |
| 5,438,109 | A | | 8/1995 | Nugent, Jr. et al. | ......... 525/526 |
| 5,658,668 | A | * | 8/1997 | Kobayashi et al. | ......... 428/418 |
| 2002/0120063 | A1 | * | 8/2002 | Kutsuna et al. | ............. 525/107 |
| 2004/0044147 | A1 | * | 3/2004 | Kamae et al. | ............... 525/523 |
| 2004/0059085 | A1 | * | 3/2004 | Shimoda et al. | ............ 528/408 |

FOREIGN PATENT DOCUMENTS

WO    WO 02/066536 A1 *  8/2002

OTHER PUBLICATIONS

Abstract of WO 02/081540 A1.*

\* cited by examiner

*Primary Examiner*—Michael J. Feely
(74) *Attorney, Agent, or Firm*—Woodcock Washburn LLP

(57) ABSTRACT

The present invention relates to polyepoxy resins, methods for making polyepoxy resins water soluble, curable coating compositions, and kits useful in their preparation.

19 Claims, No Drawings

POLYEPOXY RESIN COMPOSITIONS

FIELD OF THE INVENTION

The present invention relates to polyepoxy resins, methods for making polyepoxy resins water soluble, curable coating compositions, and kits useful in their preparation.

BACKGROUND OF THE INVENTION

Due to environmental and regulatory concerns, there is a need for water-based systems to manufacture polymeric coatings. Typically, polyepoxy resins and their polyamine curative agents (or resultant products) have had relatively limited solubility in water or mixed water/solvent systems, giving rise to multi-phase reactions and application systems. To overcome this, surfactants are commonly employed to provide a more continuous phase. Illustrative examples of polyepoxy resin coatings prepared in water and non-water based systems can be found in U.S. Pat. No. 4,014,830 and U.S. Pat. No. 5,438,109.

Frequently, high levels of surfactant are required. Use of surfactants in multi-phase systems, especially at higher levels, has the disadvantage of reducing performance and stability of the resultant polymers by adversely impacting film properties such as gas permeability, hardness, gloss, abrasion resistance, imperviousness to water, and the like. Moreover, coalescence of the reactants caused by the general nature of surfactant based systems, may, as the system dries, give rise to surface irregularities which also influence coating performance, such as arcing in electrical-coating-based applications.

Therefore, what is needed is a water-based system to manufacture polymeric coatings which generally does not require surfactants, although such surfactants may be utilized. The invention herein described is directed to these and other important ends.

SUMMARY OF THE INVENTION

In one embodiment, the invention provides a method for making a polyepoxy resin water soluble, comprising contacting said resin with a carboxylic acid.

In another embodiment, the invention provides a compound of formula I:

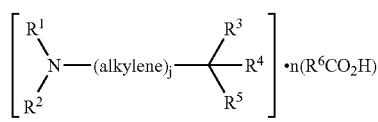

wherein:
$R^1$ and $R^2$ are each independently alkyl or -(alkylene)-epoxyethyl;
$R^3$ is alkyl, aralkyl, or aryl, wherein said alkyl, aralkyl or aryl is optionally substituted with 0-5 Z;
$R^4$ and $R^5$ are each independently H, alkyl, or aryl, wherein said alkyl or aryl is optionally substituted with 0-5 Z;
$R^6$ is H, alkyl, aryl or aralkyl;
Z is:

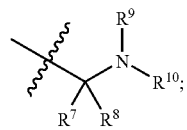

$R^7$ and $R^8$ are each independently H, alkyl, or aryl;
$R^9$ and $R^{10}$ are each independently alkyl or -(alkylene)-epoxyethyl;
j is the integer 0 or 1;
n is a number in the range from about 0.8Y to about Y; and
Y is the number of amine nitrogen atom equivalents in said compound;
provided that at least two of $R^1$, $R^2$, $R^9$ and $R^{10}$ are -(alkylene)-epoxyethyl.

In another embodiment, the invention provides a compound of formula II:

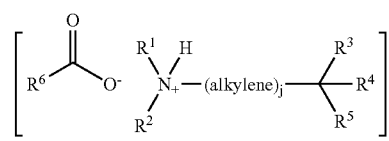

wherein:
$R^1$ and $R^2$ are each independently alkyl or -(alkylene)-epoxyethyl;
$R^3$ is alkyl, aralkyl, or aryl, wherein said alkyl, aralkyl or aryl is optionally substituted with 0-5 Z;
$R^4$ and $R^5$ are each independently H, alkyl, or aryl, wherein said alkyl or aryl is optionally substituted with 0-5 Z;
$R^6$ is H, alkyl, aryl or aralkyl;
Z is:

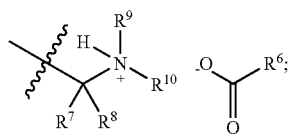

$R^7$ and $R^8$ are each independently H, alkyl, or aryl;
$R^9$ and $R^{10}$ are each independently alkyl or -(alkylene)-epoxyethyl;
j is the integer 0 or 1;
provided that at least two of $R^1$, $R^2$, $R^9$ and $R^{10}$ are -(alkylene) epoxyethyl.

In another embodiment, the invention provides a compound of formula IIA:

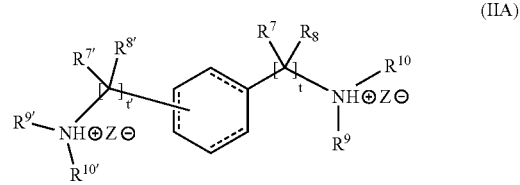

wherein:
t is 1, 2, 3, 4, 5, or 6;
t' is 1, 2, 3, 4, 5, or 6;
$R^7$, $R^{7'}$, $R^8$, and $R^{8'}$ are each independently H, alkyl, or aryl;
$R^9$, $R^{9'}$, $R^{10}$, and $R^{10'}$ are each independently alkyl or -(alkylene)-epoxyethyl; and
Z is the anion of a weak acid.

In another embodiment, the invention provides a polyepoxy resin composition comprising a compound of formula III:

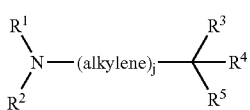

wherein:
$R^1$ and $R^2$ are each independently alkyl or -(alkylene)-epoxyethyl;
$R^3$ is alkyl, aralkyl, or aryl, wherein said alkyl, aralkyl or aryl is optionally substituted with 0-5 Z;
$R^4$ and $R^5$ are each independently H, alkyl, or aryl, wherein said alkyl or aryl is optionally substituted with 0-5 Z;
Z is:

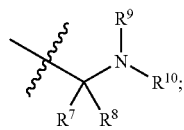

$R^7$ and $R^8$ are each independently H, alkyl, or aryl;
$R^9$ and $R^{10}$ are each independently alkyl or -(alkylene)-epoxyethyl;
j is the integer 0 or 1;
provided that at least two of $R^1$, $R^2$, $R^9$ and $R^{10}$ are -(alkylene) epoxyethyl; and
a carboxylic acid.

These and other aspects of the invention will become more apparent from the present description and claims.

DETAILED DESCRIPTION OF ILLUSTRATIVE EMBODIMENTS

The present invention relates to polyepoxy resins, methods for making polyepoxy resins water soluble, curable coating compositions, and kits useful in their preparation.

Accordingly, in one embodiment, the invention provides a method for making a polyepoxy resin water soluble, comprising contacting said polyepoxy resin with a carboxylic acid. In some embodiments, methods of the invention enhance the level of water solubility of polyepoxy resins and, as such, may either expand the range of polyepoxy resins which may be utilized in partially or completely aqueous formulations, including but not limited to those polyepoxy resins which are typically insoluble in aqueous-based systems, improve their overall performance, or simplify processes in which the methods of the invention are employed.

Preferably, the carboxylic acid contacting said resin is water soluble. More preferably, the carboxylic acid contacting said resin is acetic acid.

As used herein, the term "polyepoxy resin" refers to monomeric or oligomeric thermosetting resins whose reactivity is dependent on two or more epoxide moieties within the monomeric or oligomeric resin structure. Oligomeric resins typically have from about 0 to about 6 repeating monomer units. Preferably the oligomeric resins typically have from about 0 to about 2 repeating units.

Polyepoxy resins are substituted with one or more —N(R)$_2$ moieties, wherein each R group is independently alkyl, aryl, aralkyl, or -alkylene-epoxyethyl provided that at least two of R are independently -alkylene-epoxyethyl, and include but are not limited to meta-xylene diamine polyepoxy resins and 1,3-cyclohexane diamine polyepoxy resins. Non-limiting examples of polyepoxy resins include those bearing one —N(R)$_2$ moiety, such as benzyl-bis-oxiranyl-methyl-amine and those bearing more than one —N(R)$_2$ moiety, such as the meta-xylene polyepoxy resins methyl-{3-[(methyl-oxiranylmethyl-amino)-methyl]-benzyl}-oxiranylmethyl-amine and {3-[(Bis-oxiranylmethyl-amino)-methyl]-benzyl}-bis-oxiranylmethyl-amine, the latter being commercially available as "ERISYS GA-240" (CVC Specialty Chemicals Inc., Maple Shade, N.J.), and the hexahydro-meta-xylene polyepoxy resin {3-[(Bis-oxiranylmethyl-amino)-methyl]-cyclohexylmethyl}-bis-oxiranylmethyl-amine, commercially available as "TETRAD C" (Mitsubishi Gas Chemical Co., New York, N.Y.).

In another embodiment, the invention provides novel polyepoxy resin compounds of formula I:

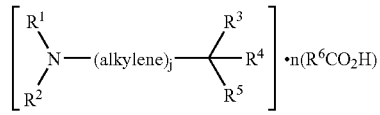

wherein:
$R^1$ and $R^2$ are each independently alkyl or -(alkylene)-epoxyethyl;
$R^3$ is alkyl, aralkyl, or aryl, wherein said alkyl, aralkyl or aryl is optionally substituted with 0-5 Z;
$R^4$ and $R^5$ are each independently H, alkyl, or aryl, wherein said alkyl or aryl is optionally substituted with 0-5 Z;
$R^6$ is H, alkyl, aryl or aralkyl;
Z is:

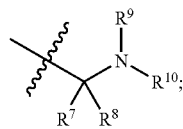

$R^7$ and $R^8$ are each independently H, alkyl, or aryl;
$R^9$ and $R^{10}$ are each independently alkyl or -(alkylene)-epoxyethyl;
j is the integer 0 or 1;
n is a number in the range from about 0.8Y to about Y (and all combinations and subcombinations therein); and
Y is the number of amine nitrogen atom equivalents in said compound;
provided that at least two of $R^1$, $R^2$, $R^9$ and $R^{10}$ are -(alkylene)-epoxyethyl.

In a preferred embodiment, $R^1$ and $R^2$ are each independently alkyl or -(alkylene)-epoxyethyl, more preferably $R^1$ and $R^2$ are each -(alkylene)-epoxyethyl. In a preferred embodiment, the alkylene portion of $R^1$ and $R^2$ is —$CH_2$—.

In embodiments where $R^3$ is alkyl, said alkyl may preferably be cyclohexyl. More preferably, where $R^3$ is cyclohexyl, $R^3$ is:

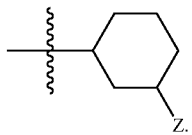

In embodiments where $R^3$ is aryl, said aryl may preferably be phenyl. More preferably, when $R^3$ is phenyl, $R^3$ is:

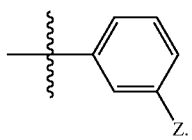

In some embodiments, $R^4$ and $R^5$ are each independently H or alkyl, more preferably, each of $R^4$ and $R^5$ is H.

In some embodiments, $R^6$ is H or $C_1$-$C_8$ alkyl. When $R^6$ is $C_1$-$C_8$ alkyl, $R^6$ is preferably $C_1$-$C_4$ alkyl, and more preferably $R^6$ is methyl.

In some embodiments, $R^7$ and $R^8$ are each independently H or alkyl. Preferably, at least one of $R^7$ and $R^8$ is H, and more preferably, each of $R^7$ and $R^8$ is H. In certain other preferred embodiments, $R^7$ and $R^8$ are each H and Z is —$CH_2NR^9R^{10}$.

In some embodiments, $R^9$ and $R^{10}$ are each independently alkyl or -(alkylene)-epoxyethyl. In a preferred embodiment, the alkylene portion of $R^9$ or $R^{10}$ is —$CH_2$—. In a preferred embodiment, $R^9$ and $R^{10}$ are each —($CH_2$)-epoxyethyl.

In a preferred embodiment, $R^1$, $R^2$, $R^9$ and $R^{10}$ are each -(alkylene)-epoxyethyl, more preferably —($CH_2$)-epoxyethyl.

In a preferred embodiment, j is the integer 0.

In a preferred embodiment, n is a number in the range from about 0.9Y to about Y. Even more preferably, n is a number having a value of about Y.

In a preferred embodiment, the compound of formula I is substantially water soluble.

In another embodiment, the invention provides novel polyepoxy resin compounds of formula II:

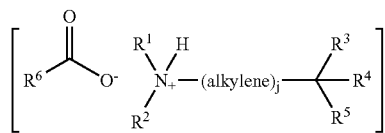

wherein:
  $R^1$ and $R^2$ are each independently alkyl or -(alkylene)-epoxyethyl;
  $R^3$ is alkyl, aralkyl, or aryl, wherein said alkyl, aralkyl or aryl is substituted with 0-5 Z;
  $R^4$ and $R^5$ are each independently H, alkyl, or aryl, wherein said alkyl or aryl is optionally substituted with 0-5 Z;
  $R^6$ is H, alkyl, aryl or aralkyl;

Z is:

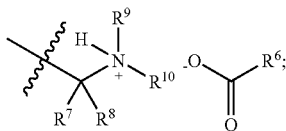

$R^7$ and $R^8$ are each independently H, alkyl, or aryl;
  $R^9$ and $R^{10}$ are each independently alkyl or -(alkylene)-epoxyethyl;
  j is the integer 0 or 1;
  provided that at least two of $R^1$, $R^2$, $R^9$ and $R^{10}$ are -(alkylene)-epoxyethyl.

In a preferred embodiment, $R^1$ and $R^2$ are each independently alkyl or -(alkylene)-epoxyethyl, more preferably $R^1$ and $R^2$ are each -(alkylene)-epoxyethyl. In a preferred embodiment, the alkylene portion of $R^1$ and $R^2$ is —$CH_2$—.

In embodiments where $R^3$ is alkyl, said alkyl may preferably be cyclohexyl.

More preferably, where $R^3$ is cyclohexyl, $R^3$ is:

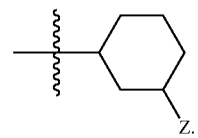

In embodiments where $R^3$ is aryl, said aryl may preferably be phenyl. More preferably, when $R^3$ is phenyl, $R^3$ is:

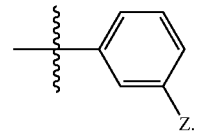

In some embodiments, $R^4$ and $R^5$ are each independently H or alkyl, more preferably, each of $R^4$ and $R^5$ is H.

In some embodiments, $R^6$ is H or $C_1$-$C_8$ alkyl. When $R^6$ is $C_1$-$C_8$ alkyl, $R^6$ is preferably $C_1$-$C_4$ alkyl, and more preferably $R^6$ is methyl.

In some embodiments, $R^7$ and $R^8$ are each independently H or alkyl. Preferably, at least one of $R^7$ and $R^8$ is H, and more preferably, each of $R^7$ and $R^8$ is H. In certain other preferred embodiments, $R^7$ and $R^8$ are each H wherein Z is:

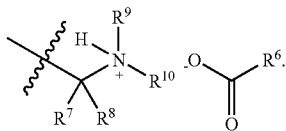

In some embodiments, $R^9$ and $R^{10}$ are each independently alkyl or -(alkylene)-epoxyethyl. In a preferred embodiment, the alkylene portion of $R^9$ or $R^{10}$ is —$CH_2$—. In a preferred embodiment, $R^9$ and $R^{10}$ are each —($CH_2$)-epoxyethyl.

In a preferred embodiment, $R^1$, $R^2$, $R^9$ and $R^{10}$ are each -(alkylene)-epoxyethyl, more preferably —($CH_2$)-epoxyethyl.

In a preferred embodiment, j is the integer 0.

In a preferred embodiment, the compound of formula II is substantially water soluble.

In another embodiment, the invention provides novel polyepoxy resin compounds of formula IIA:

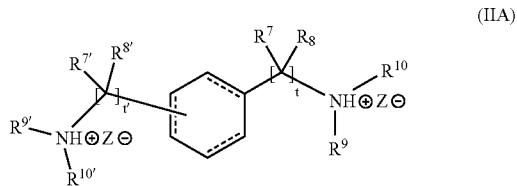

wherein:
t is 1, 2, 3, 4, 5, or 6;
t' is 1, 2, 3, 4, 5, or 6;
$R^7$, $R^{7'}$, $R^8$, and $R^{8'}$ are each independently H, alkyl, or aryl;
$R^9$, $R^{9'}$, $R^{10}$, and $R^{10'}$ are each independently alkyl or -(alkylene)-epoxyethyl; and
Z is the anion of a weak acid.

It is understood that a dashed line represents that there may be either a single bond or a double bond present.

A "weak acid" is an acid that partially disassociates in water. Weak acids include carboxylic acids, such as acetic acid, as well as hydrofluoric acid, acetylsalicylic acid, nicotinic acid, and others well-known in the art. Acetic acid is preferred.

In a preferred embodiment, $R^7$, $R^{7'}$, $R^8$, and $R^{8'}$ are each H, and t and t' are each 1.

In another preferred embodiment, the six-membered ring is meta-substituted.

In another preferred embodiment, the six-membered ring is phenyl.

In another embodiment, the invention provides novel polyepoxy resin compositions comprising a compound of formula III:

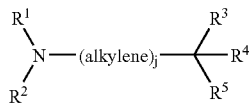

wherein:
$R^1$ and $R^2$ are each independently alkyl or -(alkylene)-epoxyethyl;
$R^3$ is alkyl, aralkyl, or aryl, wherein said alkyl aralkyl or aryl is optionally substituted with 0-5 Z;
$R^4$ and $R^5$ are each independently H, alkyl, or aryl, wherein said alkyl or aryl is optionally substituted with 0-5 Z;
Z is:

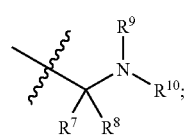

$R^7$ and $R^8$ are each independently H, alkyl, or aryl;
$R^9$ and $R^{10}$ are each independently alkyl or -(alkylene)-epoxyethyl;
j is the integer 0 or 1;
provided that at least two of $R^1$, $R^2$, $R^9$ and $R^{10}$ are -(alkylene) epoxyethyl; and
a carboxylic acid.

In a preferred embodiment, the ratio of carboxylic acid equivalents to amine nitrogen atom equivalents is a number within the range of about 0.8 to about 5 (and all combinations and subcombinations therein). More preferably, said ratio is a number within the range of about 0.8 to about 1.5.

In a preferred embodiment, $R^3$ is aryl, wherein $R^7$ and $R^8$ are each H, wherein Z is —$CH_2NR^9R^{10}$, and wherein each of $R^1$, $R^2$, $R^9$, and $R^{10}$ is:

More preferably, $R^3$ is:

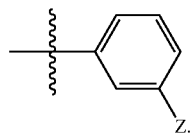

In another preferred embodiment, $R^3$ is alkyl, wherein $R^7$ and $R^8$ are each H, wherein Z is —$CH_2NR^9R^{10}$, and wherein each of $R^1$, $R^2$, $R^9$, and $R^{10}$ is:

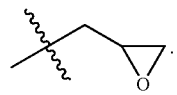

More preferably, $R^3$ is:

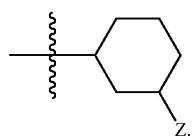

In yet another preferred embodiment, the composition is substantially water soluble.

In yet another preferred embodiment, the composition further comprises water.

Compounds and compositions of the invention may find use in coating applications where the use of water-based, mixed water/solvent, and solvent borne systems are currently practiced. Typical applications include but are not limited to coatings for concrete and metal, barrier coatings for reducing the permeability of plastic packaging materials, dip baths for electrical lamination and coatings among others. The use of compounds and compositions of the invention and their formulations reduces induction time required prior to application of the coating formulations as compared to currently practiced methods, extends pot life of the formulation over that currently practiced, and provides substantially flaw-free films with improved gloss characteristics.

Accordingly, in yet another embodiment, the invention provides novel coatings produced from a mixture comprising:
 a compound of formula III;
 a carboxylic acid;
 water; and
 a curative.

In a preferred embodiment, the carboxylic acid is acetic acid.

In a preferred embodiment, the compound of formula III is:

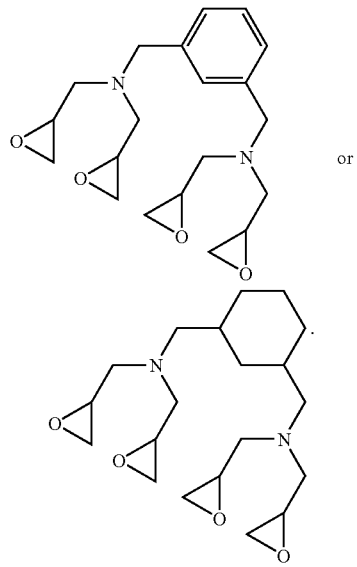

or

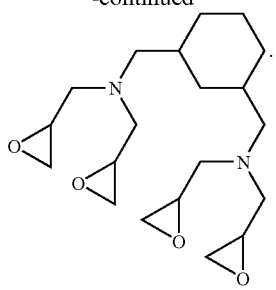

and more preferably:

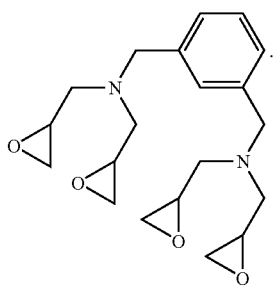

In yet another embodiment, the invention provides a kit for forming a coating produced from a mixture comprising:
 a compound of formula III; and
 a carboxylic acid.

In a preferred embodiment, the carboxylic acid is acetic acid.

In a preferred embodiment, the compound of formula III is:

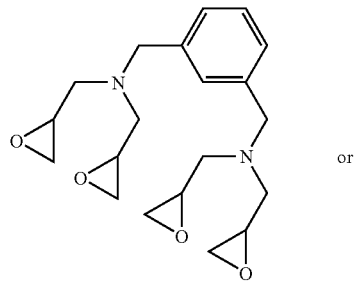

or and more preferably:

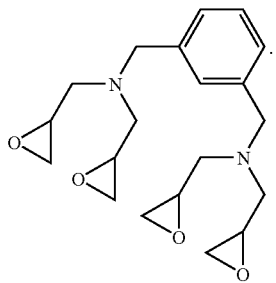

In a preferred embodiment, the kit further comprises at least one of water and a curative.

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 10 carbon atoms (and all combinations and subcombinations of ranges and specific numbers of carbon atoms therein. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkylene" refers to a bivalent alkyl radical having the general formula —$(CH_2)_n$-, where n is an integer from about one to about twenty. More preferably, n is an integer from about one to about ten. Non-limiting examples include methylene, trimethylene, pentamethylene, and hexamethylene. Alkylene groups may also contain one or more double or triple bonds within the backbone of the —$(CH_2)_n$— moiety, provided that the resultant compound is stable. Non-limiting examples include —$CH_2$—C≡C—$CH_2$— and —$CH_2$—CH=CH—$CH_2$—. Alkylene groups can be substituted or unsubstituted.

As used herein, the term "amine nitrogen atom equivalents" refers to the number of unprotonated electron lone pair equivalents on nitrogen atoms within a compound that are capable of being protonated by an acid moiety. As a non-limiting example, N,N,N',N'-tetramethyl ethylene diamine has two amine nitrogen atom equivalents, one at each of the trisubstituted amine moieties, whereas benzyl trimethylammonium chloride has 0 amine nitrogen atom equivalents.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred, wherein alkyl and aryl are as defined hereinabove. Aralkyl groups can be optionally substituted. Non-limiting examples include, for example, benzyl, diphenylmethyl, triphenylmethyl, α-naphthylmethyl, α-phenylethyl, β-phenylethyl and diphenylethyl.

As used herein, the term "carboxylic acid" refers to a moiety of general formula RC(=O)OH, wherein R is hydrogen or alkyl and wherein alkyl is as defined hereinabove. Preferably, R is $C_1$-$C_6$ alkyl. More preferably, R is $C_1$-$C_3$ alkyl. Even more preferably R is $CH_3$.

As used herein, the term "coating" refers to a thin film covering over a substrate applied for the purpose of substrate protection or improved surface appearance.

As used herein, the term "contacting" refers to the bringing together of compounds to within distances that allow for intermolecular interactions and chemical transformations accompanying such interactions. Often, contacting compounds are in solution phase.

As used herein, the term "curative" refers to a catalytic pr reactive agent which when added to a resin causes polymerization of that resin.

As used herein, the term "epoxyethyl" refers to a

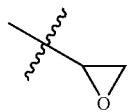

moiety.

Typically, substituted chemical moieties include one or more substituents that replace hydrogen. Exemplary substituents include, for example, halo (e.g., —F, —Cl,), alkoxy, monohaloalkoxy, polyhaloalkoxy, alkyl, aralkyl, aryl, hydroxyl (—OH), nitro (—$NO_2$), cyano (—CN), sulfonyl (—$SO_2R^4$), sulfamoyl (—$SO_2NR^5R^6$), amino (—NH2, $NHR^5$, $NHR^6$, $N(R^5R^6)$) and the like.

"Stable compound" is meant to indicate a compound that is sufficiently robust to survive isolation to a useful degree of purity from a reaction mixture, and formulation into a composition, or kit. Stable compounds are preferred in accordance with the present invention.

As used herein, the term "substantially water soluble" refers to the capability of a given amount of a compound to dissolve in water to an extent of about 75%. More preferably, about 80% of the compound dissolves. Even more preferably, about 85% of the compound dissolves. Yet more preferably, about 90% dissolves. More preferably still, about 95% dissolves. Even more preferably, about 98% dissolves. Most preferably, the compound completely dissolves in water.

When any variable occurs more than one time in any constituent or in any formula, its definition in each occurrence is independent of its definition at every other occurrence. Thus, for example, if an $R^3$ group is shown to be substituted with, for example, 1 to 5 of —CN, —$OCF_3$, mono- or polyhaloalkoxy, —$NR^5R^6$, —$SO_2R^4$, or —$SO_2NR^5R^6$, then said $R^3$ group may optionally be substituted with up to five of the above mentioned substituents, and the substituent at each occurrence is selected independently from the above defined list of possible substituents.

Combinations of substituents and/or variables are permissible only if such combinations result in stable compounds. It is further understood that, while certain substituents are minimally required, such as, for example in the $R^1$ moiety, the moiety may be further substituted with the same substituent(s), another substituent(s) from the group of required substituents, or other substituent(s) not from the group of required substituents.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way. Additional objects, advantages, and novel features of this invention will become apparent to those skilled in the art upon examination of the following examples thereof, which are not intended to be limiting.

EXAMPLES

Testing Procedures

Epoxy equivalent weight (EEW) values were determined by employing ASTM Method D 1652 "Standard Test Methods for Epoxy Content of Epoxy Resins". Amine Values were determined using ASTM Method D 2074-92 "Standard Test Method for Total, Primary, Secondary and Tertiary Amine Values of Fatty Amines by Alternative Indicator Method". Extent of water solubility was determined using ASTM Method E1148 "Solubility of Organic Compounds in Water". Tack Free Time or Set to Touch Time was determined by employing ASTM Method D1650-91 "Standard Test Methods of Sampling and Testing Shellac Varnish". The Amine Hydrogen Equivalent Weight (AHEW) value was provided by the supplier of the curative. Coating gloss and appearance characteristics were established by visual observation.

General Conditions for all reactions and testing procedures were 25° C. and 50% relative humidity.

Example 1

Preparation of Parts A (Water Soluble Epoxy), and B1 and B2 (Curatives)

Part A (Water Soluble Epoxy): A water soluble epoxy was prepared by adding 14.2 parts (0.24 moles) of glacial acetic acid at room temperature to a mixture of 50 parts (0.12 moles) of {3-[(Bis-oxiranylmethyl-amino)-methyl]-benzyl}-bis-oxiranylmethyl-amine (ERISYS GA-240 (CVC Specialty Chemicals Inc., Maple Shade, N.J.)), and 50 parts of water in a 250 mL Erlenmeyer flask. After about 5 minutes of mixing a complete solution was obtained. The epoxy equivalent weight (EEW) of the resulting solution was 239. The calculated theoretical EEW based on the EEW of the ERISYS GA-240 was 235.

Part B1 (Water Soluble Curative): Curative B1 was prepared by mixing 49 parts of ANQUAMINE 401 Curing Agent (Air Products and Chemicals, Inc., Allentown, Pa.) having a reported amine hydrogen equivalent weight (AHEW) of 200 with 51 parts of water. The resulting solution had a calculated AHEW of 408.

Part B2 (Water Soluble Curative): Curative B2 was prepared by mixing 49 parts of ANQUAMINE 419 Curing Agent (from Air Products and Chemicals, Inc.) having a reported AHEW of 284 with 51 parts of water. The resulting solution had a calculated AHEW of 580.

Example 2

Preparation of Coatings

Coating Formulation C—25 parts of B1 was mixed with 14.4 parts of A.
Coating Formulation D—25 parts of B2 was mixed with 10.1 parts of A.
Both Coating Formulations C and D were drawn down on cold rolled steel panels using a 50 mil wire bar. The draw downs were started at zero time and were continued at 30 minute intervals until the Formulations were no longer workable.
Coating Formulations C and D could still be applied easily after 6 hours with no visible end to pot life. Additionally, all draw down panels regardless of time of application exhibited extremely high gloss with absolutely no sign of surface imperfection or exudate. The zero time panel for Coating Formulation D exhibited a tack free time of 4.5 hours at 25° C. and 50% relative humidity.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A composition comprising:
   water; and
   a polyepoxy resin composition comprising
   a compound of formula III:

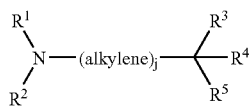

wherein:
   $R^1$ and $R^2$ are each independently alkyl or -(alkylene)-epoxyethyl;
   $R^3$ is alkyl, aralkyl, or aryl, wherein said alkyl, aralkyl or aryl is optionally substituted with 0-5 Z;
   $R^4$ and $R^5$ are each independently H, alkyl, or aryl, wherein said alkyl or aryl is optionally substituted with 0-5 Z;
   Z is:

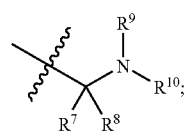

$R^7$ and $R^8$ are each independently H, alkyl, or aryl;
   $R^9$ and $R^{10}$ are each independently alkyl or -(alkylene)-epoxyethyl, provided that at least two of $R^1$, $R^2$, $R^9$ and $R^{10}$ are -(alkylene)epoxyethyl;
   j is the integer 0 or 1; and
   a carboxylic acid;
   wherein the carboxylic acid is $HCO_2H$ or alkyl-$CO_2H$, said alkyl optionally substituted with halo, alkoxy, monohaloalkoxy, polyhaloalkoxy, alkyl, aralkyl, aryl, hydroxyl (—OH), nitro (—$NO_2$), cyano (—CN), sulfonyl (—$SO_2R^4$), sulfamoyl (—$SO_2NR^5R^6$), or amino (—$NH_2$, $NHR^5$, $NHR^6$, $N(R^5R^6)$);
   wherein the polyepoxy resin composition is substantially water soluble.

2. The composition of claim 1, wherein the ratio of carboxylic acid equivalents to amine equivalents of the compound of formula III is at least about 0.8.

3. The composition of claim 2, wherein said ratio is within the range of about 0.8 to about 5.

4. The composition of claim 3, wherein $R^3$ is:

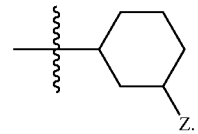

5. The composition of claim 2, wherein said ratio is within the range of about 0.8 to about 2.

6. The composition of claim 2, wherein said ratio is within the range of about 0.8 to about 1.5.

7. The composition of claim 1, wherein said aryl is:

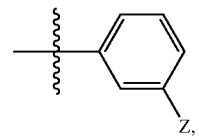

wherein $R^7$ and $R^8$ are each H, wherein Z is —$CH_2NR^9R^{10}$, and wherein each of $R^1$, $R^2$, $R^9$, and $R^{10}$ is:

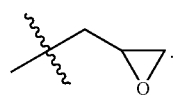

8. A coating produced from a mixture comprising: the composition of claim 1; and
   a curative.

9. The coating produced of claim 8, wherein said carboxylic acid is acetic acid.

10. The coating produced of claim 8, wherein the compound of formula III of said polyepoxy resin is:

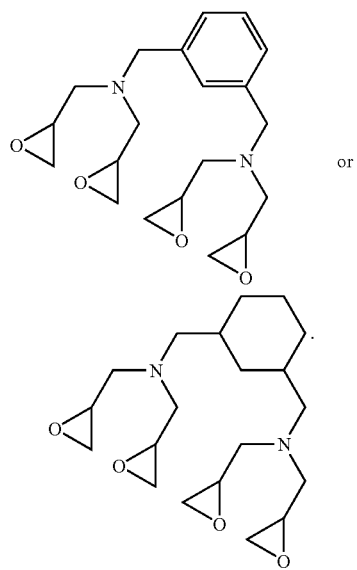

11. The coating produced of claim 10, wherein said formula III compound is:

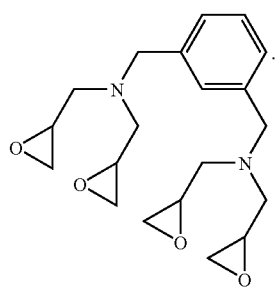

12. The coating produced of claim 11, wherein said carboxylic acid is acetic acid.

13. The coating produced of claim 10, wherein said formula III compound is:

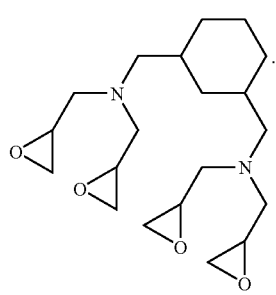

14. A kit for forming a coating produced from a mixture comprising the composition of claim 1.

15. The kit of claim 14, further comprising a curative.

16. The kit of claim 14, wherein the carboxylic acid is acetic acid.

17. The kit of claim 14, wherein the compound of formula III is:

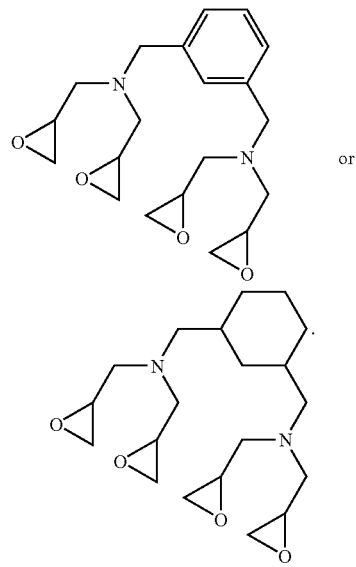

18. The kit of claim 17, wherein said formula III compound is:

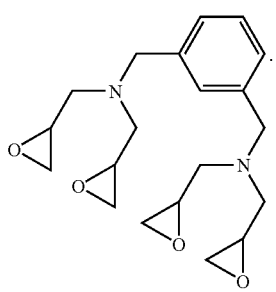

19. The kit of claim 17, wherein said formula III compound is:

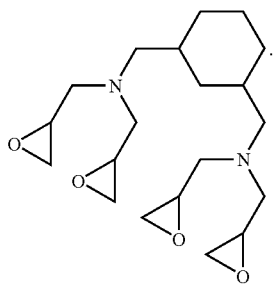

* * * * *